(12) United States Patent
Virkki et al.

(10) Patent No.: US 6,797,732 B2
(45) Date of Patent: Sep. 28, 2004

(54) PHARMACEUTICAL COMPOSITION COMPRISING ENTRACAPONE, LEVODOPA, AND CARBIDOPA

(75) Inventors: Matti Virkki, Masala (FI); Kari Vahervuo, Espoo (FI); Marja Ritala, Espoo (FI); Marja Partanen, Espoo (FI); Mervi Niskanen, Espoo (FI); Jarmo Lintulaakso, Espoo (FI); Marja Laaksonen, Masala (FI); Lasse Kervinen, Helsinki (FI); Sari Kallioinen, Espoo (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 10/223,298

(22) Filed: Aug. 20, 2002

(65) Prior Publication Data

US 2003/0017201 A1 Jan. 23, 2003

Related U.S. Application Data

(63) Continuation of application No. 09/605,529, filed on Jun. 29, 2000, now Pat. No. 6,500,867.

(30) Foreign Application Priority Data

Jun. 30, 1999 (FI) .................................................. 991485

(51) Int. Cl.[7] ........................ A01N 33/02; A61K 31/135
(52) U.S. Cl. ...................................... 514/646; 424/489
(58) Field of Search ......................... 424/489; 514/646

(56) References Cited

U.S. PATENT DOCUMENTS

| | | |
|---|---|---|
| 4,190,672 A | 2/1980 | Fahn |
| 5,389,653 A | 2/1995 | Bernauer et al. |
| 5,446,194 A | 8/1995 | Backstrom et al. |
| 5,532,274 A | 7/1996 | Wenzel et al. |

FOREIGN PATENT DOCUMENTS

| | | | |
|---|---|---|---|
| EP | 253490 | * | 6/1986 |
| EP | 0 253 490 | | 1/1988 |
| GB | 2321190 | * | 1/1997 |
| GB | 2321190 | | 7/1998 |
| WO | WO 98/31355 | | 7/1998 |
| WO | WO 98/48781 | | 11/1998 |
| WO | WO 00/15196 | | 3/2000 |
| WO | WO 01/01984 | | 1/2001 |

OTHER PUBLICATIONS

J.G. Nutt, MD et al., "Effect of peripheral catechol–O–methyltransferase inhibition on the pharmacokinetics and pharmacodynamics of levodopa in parkinsonian patients," NEUROLOGY, 44, pp. 913–919, May 1994.

Burguera et al., "Entacapone: Is it Useful as Complementary Treatment with Levodopa?," Rev Neurol 28 (8), 817–834 (1999).

(List continued on next page.)

Primary Examiner—Alton N. Pryor
(74) Attorney, Agent, or Firm—Finnegan, Henderson, Farabow, Garrett & Dunner, LLP (57) ABSTRACT

An oral solid fixed dose composition comprising pharmacologically effective amounts of entacapone, levodopa, and carbidopa, or pharmaceutically acceptable salts or hydrates thereof, and comprising at least one pharmaceutically acceptable excipient. The composition can be used, e.g., for the treatment of Parkinson's disease.

10 Claims, 6 Drawing Sheets

OTHER PUBLICATIONS

Smith et al., "Entacapone Enhances Levodopa–Induced Reversal of Motor Disability in MPTP–Treated Common Marmosets," Movement Disorders, 12(6), 935–945 (1997).

Deleu et al., "The Effect of Carbidopa and Entacapone Pretreatment on the L–Dopa Pharmacokinetics and Metabolism in Blood Plasma and Skeletal Muscle in Beagle Dog: An in Vivo Microdialysis Study," The Journal of Pharmacology and Experimental Therapeutics, 273, 1323–1331 (1995).

Ahtila et al., "Effect of Entacapone, a COMT Inhibitor, on the Pharmacokinetics and Metabolism of Levodopa After Administration of Controlled–Release Levodopa–Carbidopa in Volunteers," Clinical Neuropharmacology, 18(1), 46–57 (1995).

Davis, "Catechol–O–Methyltransferase Inhibitrors in Parkinson's Disease." CNS Drugs, vol. 10, No. 4, pp. 239–246 (1998).

Co–pending application No. 09/152,263, filed on Sep. 14, 1998.

Co–pending application No. 09/605,529, filed on Jun. 29, 2000.

* cited by examiner

PHARMACEUTICAL COMPOSITION COMPRISING ENTRACAPONE, LEVODOPA, AND CARBIDOPA

This application is a continuation of application Ser. No. 09/605,529, filed Jun. 29, 2000, now U.S. Pat. No. 6,500,867 the contents of which are specifically incorporated by reference herein, which claims the benefit of foreign priority under 35 U.S.C. §119 to Finnish patent application no. FI 991485, filed on Jun. 30, 1999. The contents of that priority document are specifically incorporated by reference herein.

FIELD OF THE INVENTION

The present invention relates to new pharmaceutical compositions comprising entacapone, levodopa, and carbidopa, or pharmaceutically acceptable salts or hydrates thereof, to a preparation method of the compositions and to a use of the compositions in a therapeutic method. The invention also relates to the use of entacapone, levodopa, and carbidopa, or their pharmaceutically acceptable salts or hydrates, in the manufacture of an oral solid fixed dose combination.

BACKGROUND OF THE INVENTION

The chemical names of entacapone, levodopa and carbidopa are (E)-2-cyano-3-(3,4-dihydroxy-5-nitrophenyl)-N,N-diethyl-2-propenamide, (−)-L-α-amino-β-(3,4-dihyroxtybenzen)propanoic acid, and (−)-L-α-hydrazino-α-methyl-β-(3,4-dihydroxybenze)propanoic acid, e.g. as the monohydrate, respectively. Entacapone is described in U.S. Pat. No. 5,446,194 as a catechol-O-methyltransferase (COMT) inhibitor. Enteral and parenteral routes of administration of entacapone are discussed in U.S. Pat. No. 5,446,194. An oral compacted composition containing entacapone and croscarmellose sodium is commercially available in the European market under the trademarks COMT-ESS® and COMTAN® manufactured by Orion Corporation, Finland. Levodopa and carbidopa are the most commonly used drugs in the treatment of Parkinson's disease. Levodopa and carbidopa are commercially available as combination tablets sold in Europe under, for instance, the following trademarks: NACOM® (distributed by DuPont Pharma), SINEMET® (distributed by Isis-Chemie), SINEMET® (distributed by DuPont Pharma), SINEMET® PLUS (distributed by DuPont Pharma in the UK) and SINEMET® LP 25 (distributed by DuPont Pharma).

Parkinsonism medication needs to be taken several times a day to keep the patients without symptoms. Therefore, patient compliance can be improved significantly by using a fixed dose combination of entacapone, levodopa, and carbidopa instead of taking two separate tablets, i.e., an entacapone tablet and a levodopa-carbidopa tablet, several times a day. This is especially important for parkinsonism patients with tremor and old age.

We have found that entacapone, levodopa, and carbidopa, or their pharmaceutically acceptable salts or hydrates, are preferably released from the oral composition as soon as possible after ingesting it.

Furthermore, it is very difficult to adjust the absorption of three different active agents from one and the same oral solid composition. Usually in practice, the absorption of one of the active agents may decrease while that of the other one increases. When selecting the pharmaceutical excipients, disintegrants and other auxiliary agents to be used in a pharmaceutical composition in combination with several active agents, numerous factors have to be considered, e.g., the chemical and physical characteristics of the active agents and the auxiliary agents, the bioavailabilities of the active agents, the method of preparing the composition, the stability of the composition, etc.

None of the above-cited patents nor any other patent or publication, of which applicants are aware, describes an oral solid composition comprising entacapone, levodopa, and carbidopa, or pharmaceutically acceptable salts or hydrates thereof.

SUMMARY OF THE INVENTION

Applicants have discovered that entacapone, levodopa and carbidopa, or their pharmaceutically acceptable salts or hydrates, can be combined into one oral solid composition with particularly interesting properties.

The invention thus provides an oral solid fixed dose composition comprising pharmacologically effective amounts of entacapone, levodopa, and carbidopa, or pharmaceutically acceptable salts or hydrates thereof, and comprising at least one pharmaceutically acceptable excipient (hereinafter referred to as a composition according to the invention), which has preferable stability and bioavailability characteristics and which is easy to swallow.

Particularly, the present invention provides an oral solid composition comprising pharmacologically effective amounts of entacapone, levodopa, and carbidopa, or pharmaceutically acceptable salts or hydrates thereof, and comprising at least one pharmaceutically acceptable excipient being a sugar alcohol, starch or sugar alcohol and starch. Preferably, the sugar alcohol is mannitol, and the starch is maize starch.

The present invention also provides a stable oral solid composition comprising pharmacologically effective amounts of entacapone, levodopa, and carbidopa, or pharmaceutically acceptable salts or hydrates thereof, and comprising at least one pharmaceutically acceptable excipient other than microcrystalline cellulose.

Applicants have found that a particularly interesting way to increase the bioavailability of carbidopa from an oral solid composition comprising entacapone, levodopa, and carbidopa is to add carbidopa separately, for instance by granulating first levodopa and entacapone together and then adding carbidopa to these granules separately.

Accordingly, the invention further provides an oral solid composition comprising pharmacologically effective amounts of entacapone, levodopa, and carbidopa, or pharmaceutically acceptable salts or hydrates thereof, and a pharmaceutically acceptable excipient, wherein a substantial portion of carbidopa is separated from entacapone and/or levodopa.

There are several different techniques to accomplish the separation of carbidopa from entacapone and levodopa, for instance, by mixing, e.g. granulating, entacapone and levodopa together and adding carbidopa separately. Carbidopa can be added as such or in a form of granules.

Therefore, the invention also provides a method for producing an oral solid pharmaceutical composition comprising pharmacologically effective amounts of entacapone, levodopa, and carbidopa, or pharmaceutically acceptable salts or hydrates thereof, and a pharmaceutically acceptable excipient, which comprises mixing first entacapone and levodopa separately and adding carbidopa separately.

The oral solid composition according to the invention includes a tablet, a capsule and the like. Preferably, the oral solid composition according to the invention is in the form of a tablet.

Furthermore, the invention provides a method for treating Parkinson's disease, e.g. at end of dose "wearing-off", by administering to a patient in need thereof an oral solid composition according to the invention, e.g. up to 8–10 times a day.

The invention also provides the use of entacapone, levodopa, and carbidopa, or pharmaceutically acceptable salts or hydrates thereof, in the manufacture of an oral solid composition for the treatment of Parkinson's disease in different stages of the disease.

Additional aspects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and do not restrict the invention, as claimed.

DETAILED DESCRIPTION OF THE INVENTION

Applicants have surprisingly discovered that an oral solid composition enabling sufficient absorption of active agents can be achieved by combining entacapone, levodopa and carbidopa, or pharmaceutically acceptable salts or hydrates thereof, in a single formulation. This has been achieved, inter alia, by improving the bioavailability and the stability of the composition, and improving the method for preparing the composition.

Applicants have found that absorptions of levodopa, carbidopa and entacapone from the digestive tract are highly variable. The bioavailabilities of levodopa and carbidopa vary both intra- and interindividually. The bioavailability of entacapone has also been extensively studied by the Applicant to arrive at the present invention.

Figure 1:
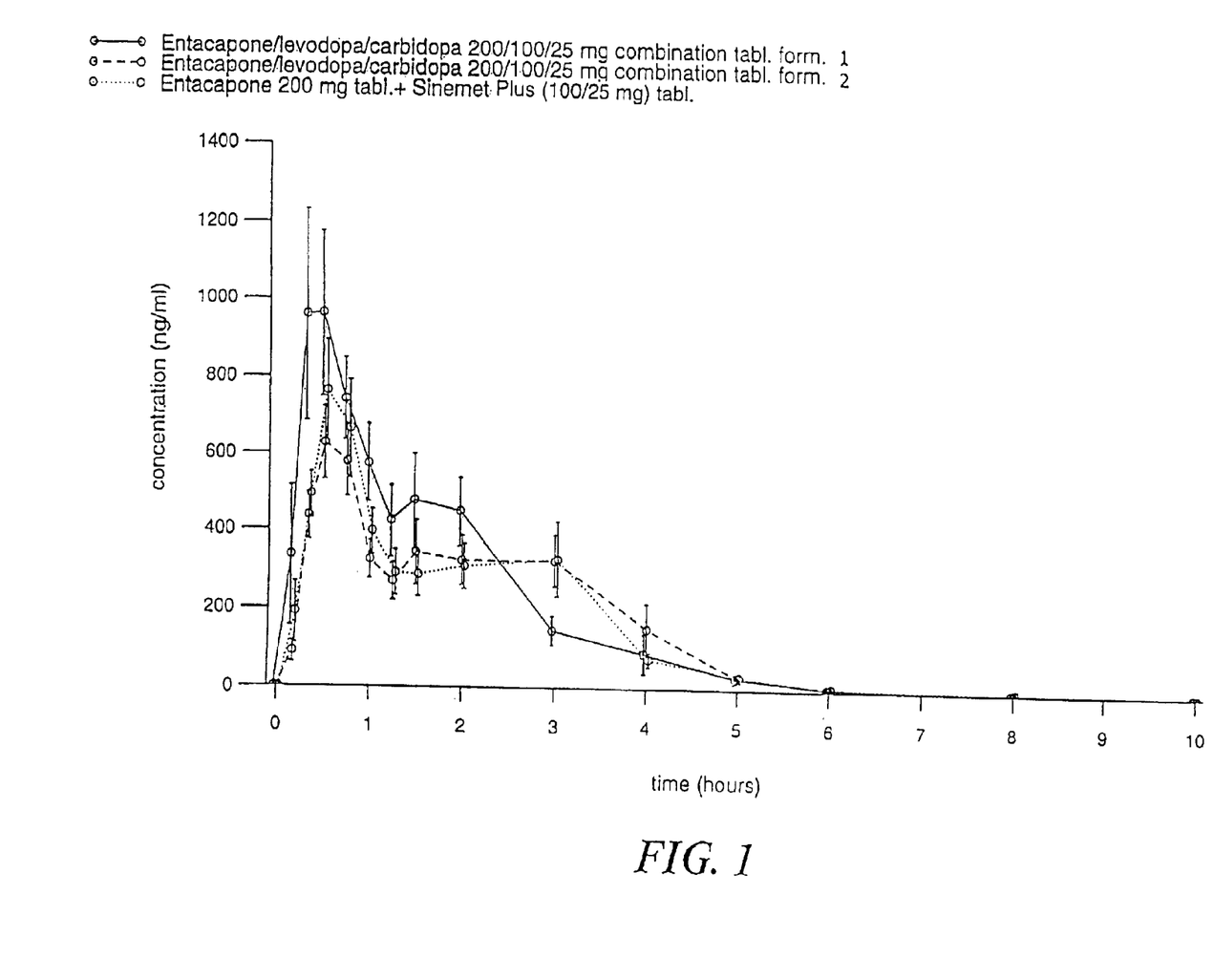
FIG. 1 shows entacapone plasma concentrations after a single oral dose of Formulation 1, Formulation 2, and a reference, which was a compacted entacapone 200 mg tablet, COMTESS®, together with a SINEMET® PLUS 100/25 tablet.
Figure 2:
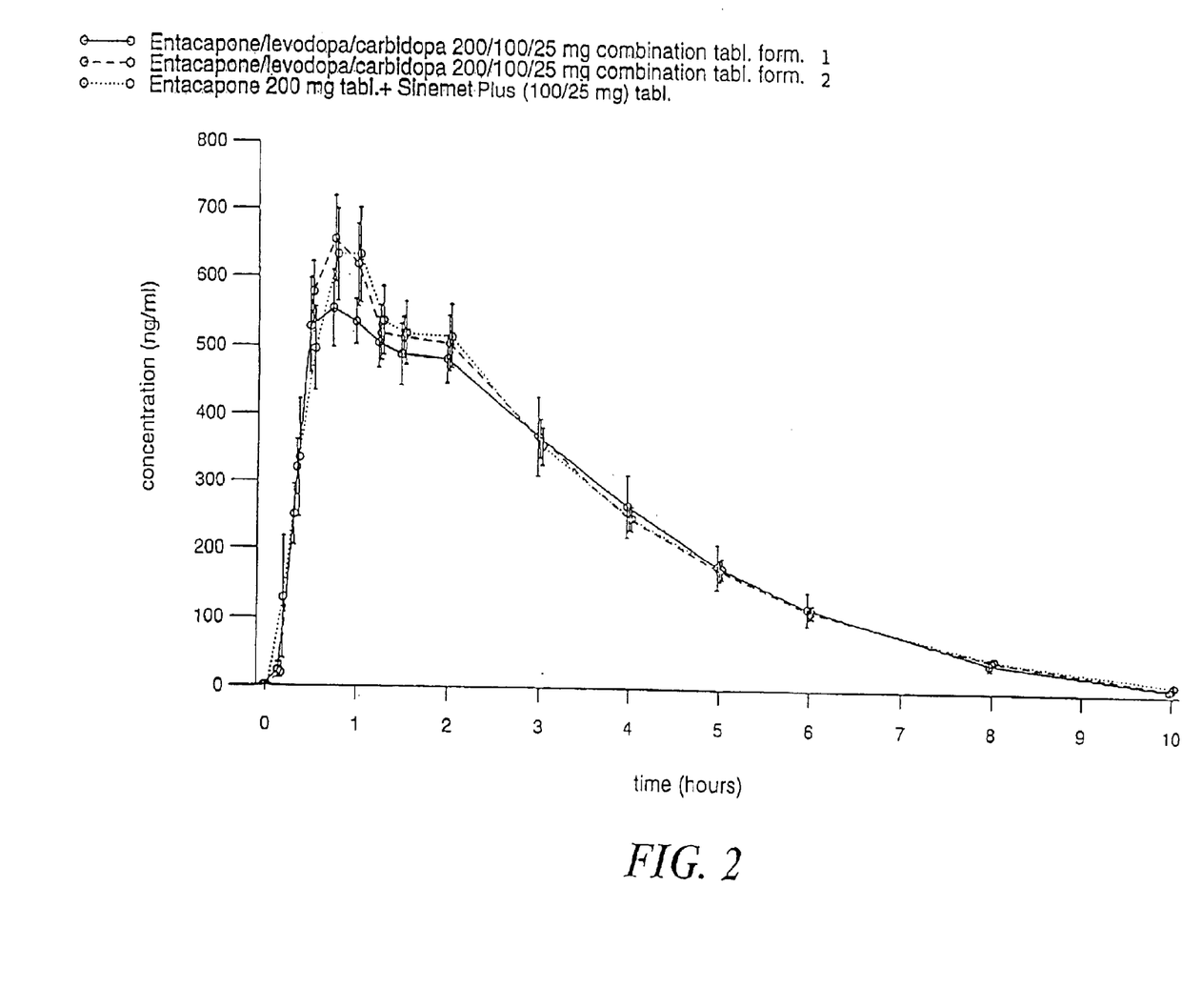
FIG. 2 shows levodopa plasma concentrations after a single oral dose of Formulation 1, Formulation 2, and a reference, which was a compacted entacapone 200 mg tablet, COMTESS®, and a SINEMET® PLUS 100/25 tablet.
Figure 3:
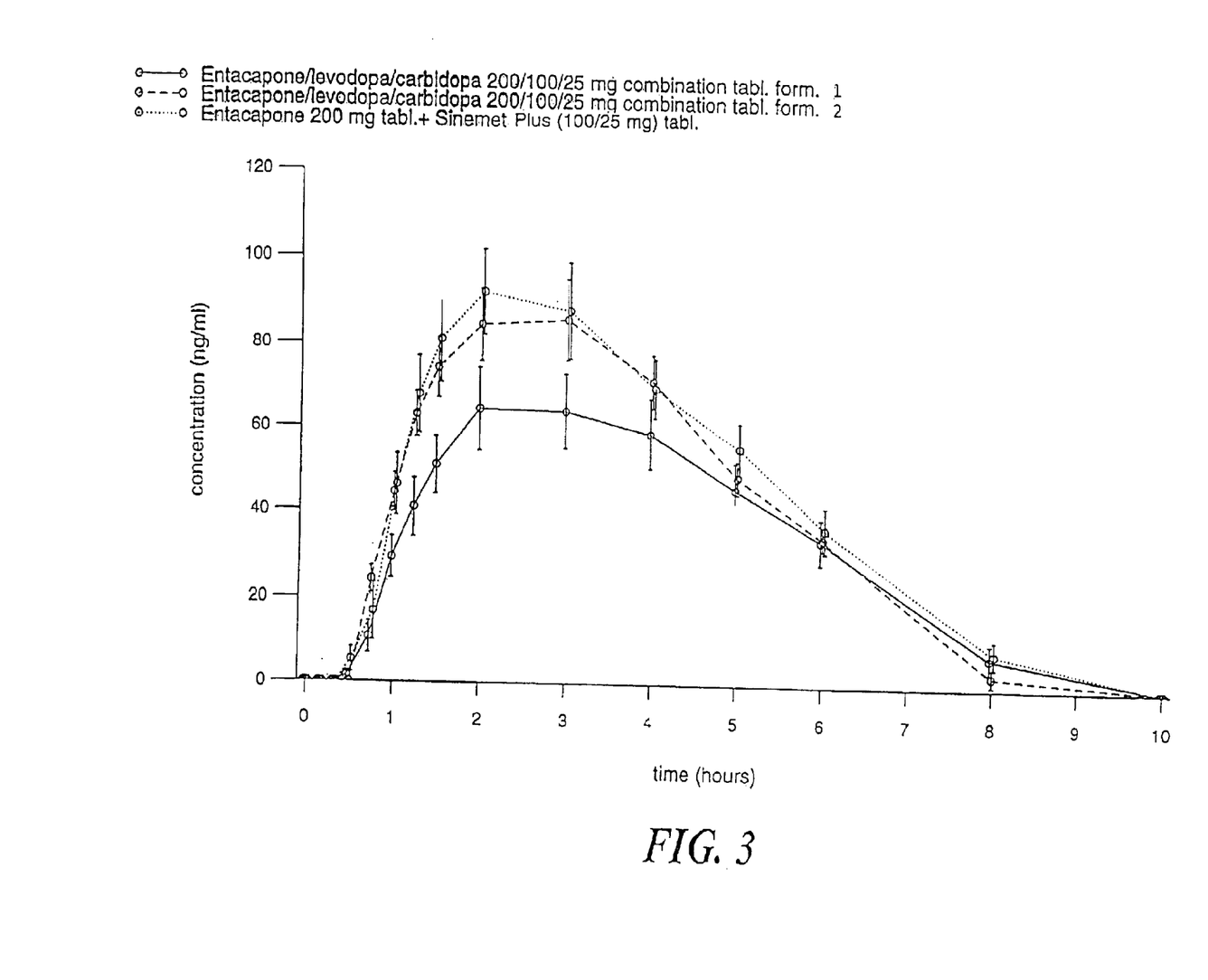
FIG. 3 shows carbidopa plasma concentrations after a single oral dose of Formulation 1, Formulation 2, and a reference, which was a compacted entacapone 200 mg tablet, COMTESS®, and a SINEMET® PLUS 100/25 tablet.

It is very challenging to harmonize the absorptions of three active agents from one and the same oral solid composition. Applicants have found that the method for preparing the composition has a significant effect on the bioavailability of carbidopa. For example, the bioavailability of carbidopa from Formulation 1 (see Example 1, Table 1), wherein all the active agents are wet granulated together, is too low compared to the reference product, SINEMET® PLUS 100/25 mg tablet. On the other hand, the bioavailability of carbidopa from Formulation 2 (see Example 1, Table 1), wherein all the active agents are dry granulated together (compaction granulated) is acceptable. However, polyethylene glycol used in Formulation 2 as a compression aid was found to cause stability problems as indicated below. The absorption data from the bioavailability studies of Formulations 1 and 2 are shown in FIGS. 1–3.

Applicants found that a preferred way to increase the bioavailability of carbidopa from an oral solid composition comprising entacapone, levodopa and carbidopa is to mix, e.g. granulate, levodopa and entacapone together and then to add carbidopa to this mixture, e.g. granules, separately.

The invention therefore provides an oral solid composition of entacapone, levodopa, and carbidopa, or pharmaceutically acceptable salts or hydrates thereof, and a pharmaceutically acceptable excipient, wherein a substantial portion of carbidopa is separated from entacapone and levodopa.

A composition of the invention, wherein "a substantial portion of carbidopa is separated from entacapone and levodopa", can preferably be obtained by mixing, e.g. granulating, entacapone and levodopa particles separately and adding carbidopa particles separately, as such or in form of granules, optionally adding one or more excipients and formulating the mixture thus formed to an oral solid composition, e.g. tablet, of the invention.

Accordingly, a preparation process for an oral solid composition of the invention is also provided, wherein carbidopa, or a pharmaceutically acceptable salt or hydrate thereof, is added separately to the composition, e.g. entacapone and levodopa are first mixed separately and carbidopa is added separately.

Entacapone and levodopa are preferably first granulated, whereby they may be granulated either separately or together. Carbidopa can be separated from entacapone and levodopa by using separate granules or by adding carbidopa extragranularly as such (in powder form) into the mixture to be formulated, e.g. into the tablet mass to be compressed. Both wet granulation and dry granulation can be used, but preferably the granulation method is wet granulation. Suitable granulation methods are known in the art. The wet granulation is preferably effected using e.g. povidone. Povidone is added as such or as an aqueous colloidal dispersion thereof.

Figure 4:
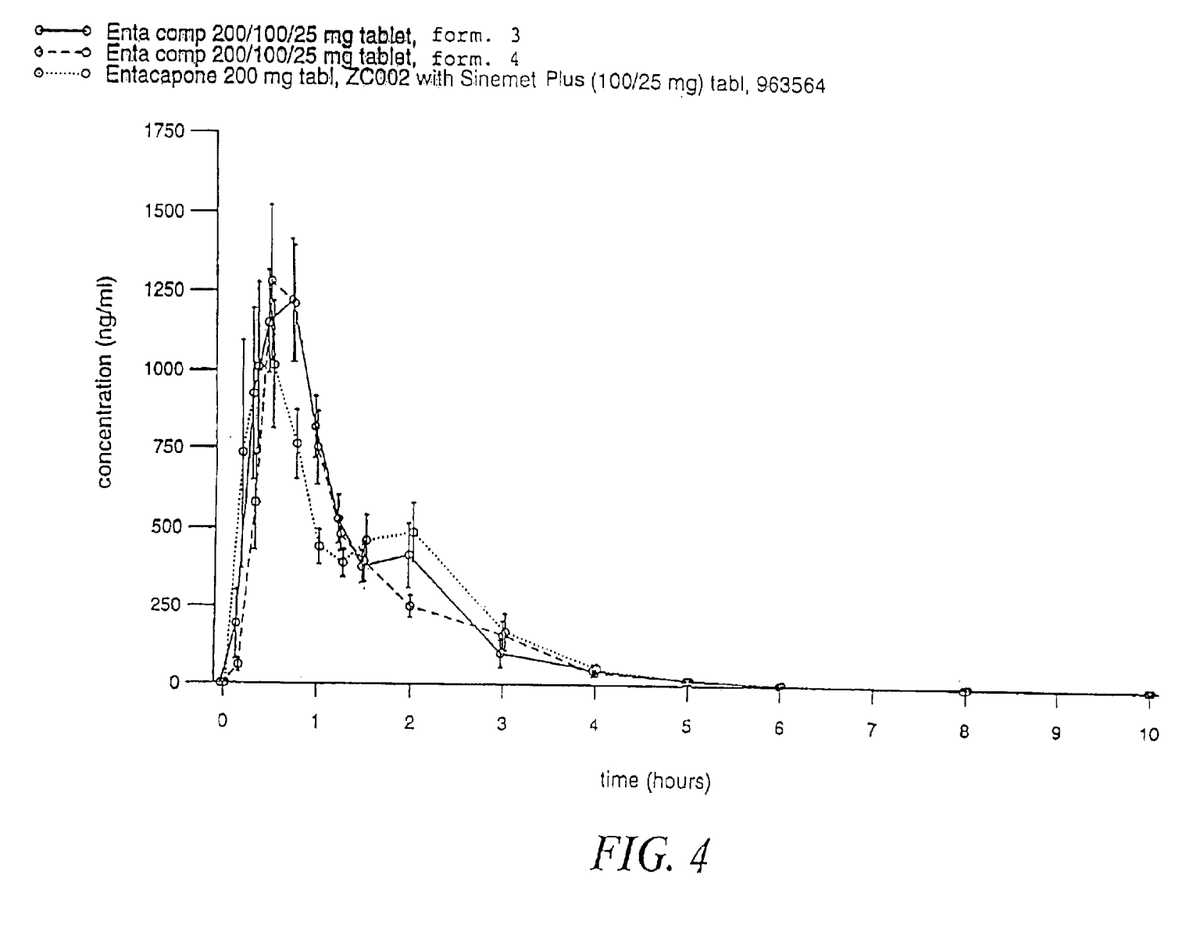
FIG. 4 shows entacapone plasma concentrations after a single oral dose of Formulation 3, Formulation 4, and a reference, which was a compacted entacapone 200 mg tablet, COMTESS®, and a SINEMET® PLUS 100/25 tablet.
Figure 5:
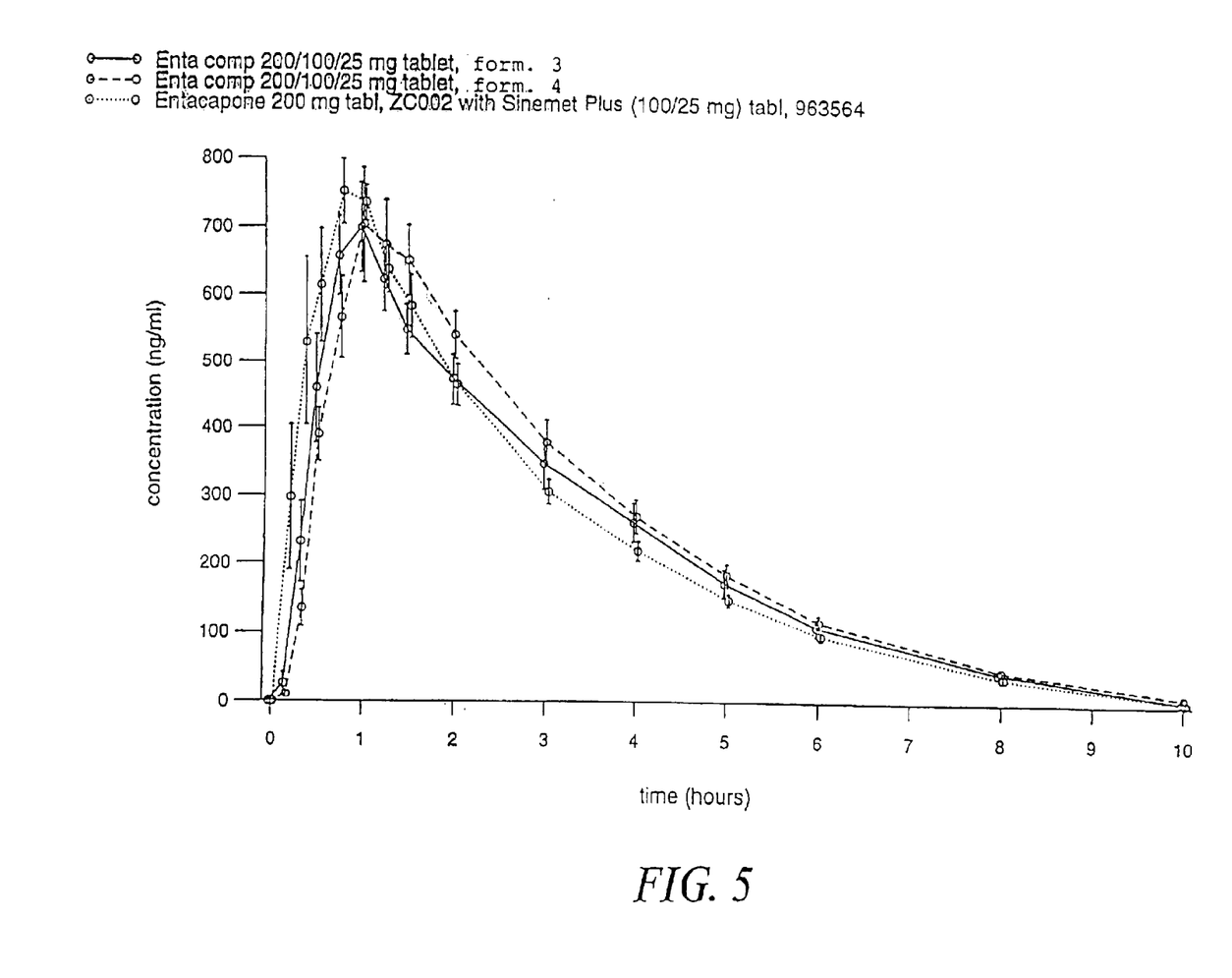
FIG. 5 shows levodopa plasma concentrations after a single oral dose of Formulation 3, Formulation 4, and a reference, which was a compacted entacapone 200 mg tablet, COMTESS®, and a SINEMET® PLUS 100/25 tablet.
Figure 6:
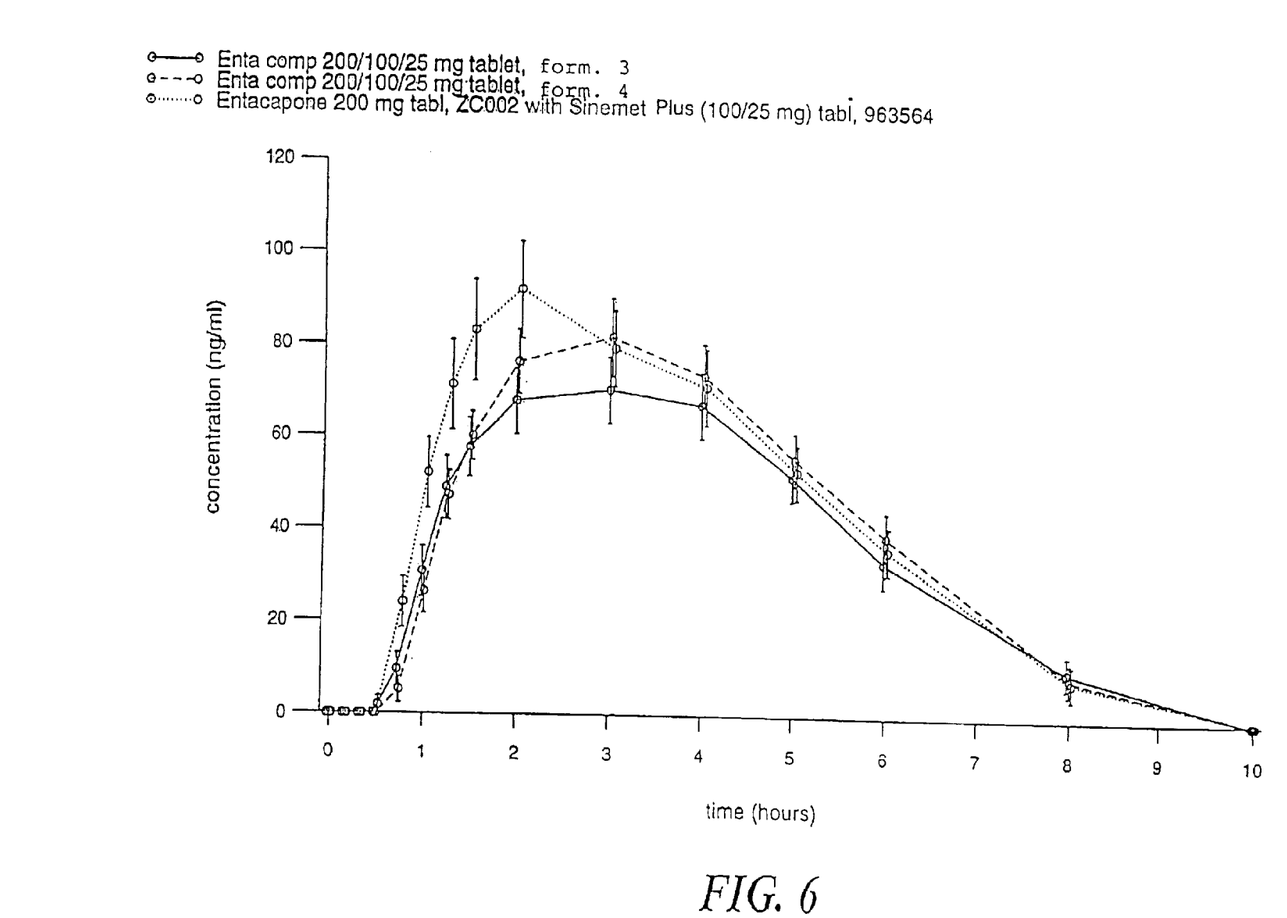
FIG. 6 shows carbidopa plasma concentrations after a single oral dose of Formulation 3, Formulation 4, and a reference, which was a compacted entacapone 200 mg tablet, COMTESS®, and a SINEMET® PLUS 100/25 tablet.

Examples of these kinds of formulations according to the invention are described in Example 2. The absorption of entacapone, levodopa and carbidopa from Formulations 3 and 4 was studied. The results in FIGS. 4–6 show that the absorption of the tested formulations is comparable to the commercial reference formulations.

As to the compatibility of the ingredients of compositions of the invention, Applicants have found that entacapone, levodopa and carbidopa are as such compatible with each other e.g. as determined using different physicochemical techniques, e.g. HPLC or microcalorimetric determination.

However, it was also found that many commonly used excipients are not suitable to be used in oral solid compositions containing entacapone, levodopa and carbidopa. Most of the levodopa-carbidopa formulations available in the market contain microcrystalline cellulose as a carrier. Also, the entacapone formulations COMTESS® and COMTAN®, which recently became available in Europe, contain considerable amounts of microcrystalline cellulose. In the prior art, microcrystalline cellulose appears to be an acceptable excipient. For compositions of the invention, however, applicants unexpectedly found that microcrystalline cellulose destabilizes the formulations on long term storage, when all three active agents are combined together.

Accordingly, the invention provides a stable oral solid pharmaceutical composition comprising pharmacologically effective amounts of entacapone, levodopa, and carbidopa, or pharmaceutically acceptable salts or hydrates thereof, and at least one pharmaceutically acceptable excipient other than microcrystalline cellulose.

Additionally, the use of polyethylene glycol as an excipient resulted in tablets which were found to be unstable in a standard stability test (see Formulation 2 in Example 1). The Applicants believe that a reason for the stability problems is the surface-activity of polyethylene glycol, which may enhance the degradation of the active substances. Other surface-active substances, e.g. polysorbate and sodium lauryl sulphate, have also been found to be incompatible with the fixed dose combination, e.g. as indicated by standard stability tests. The physicochemical tests mentioned above have also revealed incompatibilities of the drug combination with colloidal silicon oxide, copolyvidone and previously mentioned substances with surface active properties, i.e., polyethylene glycol, polysorbate and sodium lauryl sulphate.

Accordingly, as a preferred embodiment of the invention, a stable oral solid pharmaceutical composition is provided comprising pharmacologically effective amounts of entacapone, levodopa, and carbidopa, or pharmaceutically acceptable salts or hydrates thereof, and at least one pharmaceutically acceptable excipient other than microcrystalline cellulose and/or surface active agents and/or silica.

Despite the several incompatibilities found, the oral solid composition according to the invention can still surprisingly be prepared by using few compatible excipients alone or two or more together. Compatible excipients include, e.g., sugar alcohols, preferably mannitol, and starch, preferably maize starch as well as other appropriate excipients mentioned herein.

Accordingly, the present invention provides an oral solid composition comprising pharmacologically effective amounts of entacapone, levodopa, and carbidopa, or pharmaceutically acceptable salts or hydrates thereof, and comprising at least one pharmaceutically acceptable excipient being a sugar alcohol, starch or sugar alcohol and starch.

The amount of the sugar alcohol in the composition is preferably up to about 50% by weight, more preferably from about 5% to e.g. about 40% by weight, especially from about 7% to about 25% by weight. The amount of the starch in the composition is preferably up to about 50% by weight, more preferably from about 2% to e.g. about 35% by weight, especially from about 5% to about 25% by weight.

Oral solid compositions according to the invention may further comprise hydrogenated vegetable oil, preferably hydrogenated castor oil e.g. as an intragranual excipient.

Then, preferably, the amount of the hydrogenated vegetable oil in the composition is up to about 30% by weight, and e.g. at least 5% by weight, more preferably up to about 20% by weight, especially up to about 15% by weight.

The composition according to the invention preferably contains a suitable disintegrant, such as sodium starch glycolate, e.g. of MW 500,000–1,000,000 Daltons, e.g. Type A, (e.g. Primojel® from Avebe B.A.) or croscarmellose sodium (e.g. Ac-Di-Sol® from FMC Corporation). Preferably the amount of the disintegrant, when present in the composition, is up to about 10% by weight, e.g. from about 0.5% by weight to e.g. about 6% by weight, e.g. from about 2% by weight to about 6% by weight.

The composition may also contain a suitable conventional binder and/or lubricant in amounts known in the art. Examples of suitable lubricants useful in the present composition include, e.g., magnesium stearate, calcium stearate, hydrogenated vegetable oil, talc, etc.

The amount of entacapone, levodopa, and carbidopa, or their pharmaceutically acceptable salts or hydrates, in the oral composition is dependent on numerous factors known to one skilled in the art, such as, the severity of the condition of the patient, the desired duration of use, etc. The oral solid composition of the invention may also contain one or more other pharmacologically active agents. The amount of entacapone in the formulation according to the invention is preferably 25 to 400 mg, e.g. 25 to 300 mg, especially 50 to 200 mg, the amount of levodopa is preferably 25 to 300 mg, especially 50 to 250 mg, and the amount of carbidopa is preferably 5 to 75 mg, especially 10 to 50 mg.

Applicants have discovered that the following embodiment is particularly preferred, e.g. for a wide variety of patient populations, including early and late stage Parkinson patients:

a) 200 mg entacapone, 100 mg levodopa, and 25 mg carbidopa.

Other preferred embodiments include:

b) 200 mg entacapone, 50 mg levodopa, and 12.5 mg carbidopa c) 200 mg entacapone, 150 mg levodopa, and 37.5 mg carbidopa d) 200 mg entacapone, 100 mg levodopa, and 10 mg carbidopa e) 200 mg entacapone, 250 mg levodopa and 25 mg carbidopa.

As a further aspect the invention provides an oral solid fixed dose composition comprising pharmacologically effective amounts of entacapone, levodopa, and carbidopa, or pharmaceutically acceptable salts or hydrates thereof, and comprising at least one pharmaceutically acceptable excipient, whereby the therapeutic effect achieved with the composition in the treatment of Parkinson's disease is comparable, e.g. similar, to that achieved with the known separate formulations of entacapone, levodopa and carbidopa, e.g. entacapone tablets and levodopa-carbidopa tablets referred to herein, which are administered concomitantly, at the same doses of the active agents as the combination formulation of the invention.

In an embodiment of the combination composition of the invention, the composition is pharmacokinetically comparable to the known formulations, e.g. the entacapone and levodopa-carbidopa formulations used herein as a reference, administered concomitantly at the same doses of active agents as the composition of the invention. In a further embodiment, the composition of the invention is substantially bioequivalent with the known formulations, e.g. the bioavailability achieved with the composition of the invention is at levels comparable to that achieved with the concomitant administration of the same doses of the known separate formulations of entacapone, levodopa and carbidopa, e.g. the entacapone and levodopa-carbidopa formulations used herein as a reference. (See also Examples).

In preferred embodiments, a) the therapeutic effect, such as pharmacokinetics, e.g. bioavailability, achieved with a combination composition of the invention of the dose of 200 mg entacapone/ 100 mg levodopa/25 mg carbidopa is comparable to that of the known formulation of entacapone and the known formulation of levodopa-carbidopa administered concomitantly at the same doses of active agents as the present combination composition;

b) the therapeutic effect, such as pharmacokinetics, e.g. bioavailability, achieved with a combination composition of the invention of the dose of 200 mg entacapone/ 50 mg levodopa/12.5 mg carbidopa is comparable to that of the known formulation of entacapone and the known formulation of levodopa-carbidopa administered concomitantly at the same doses as the present combination composition;

c) the therapeutic effect, such as pharmacokinetics, e.g. bioavailability, achieved with a combination composition of the invention of the dose of 200 mg entacapone/ 150 mg levodopa/37.5 mg carbidopa is comparable to that of the known formulation of entacapone and the known formulation of levodopa-carbidopa administered concomitantly at the same doses as the present combination composition;

d) the therapeutic effect, such as pharmacokinetics, e.g. bioavailability, achieved with a combination composition of the invention of the dose of 200 mg entacapone/ 100 mg levodopa/10 mg carbidopa is comparable to that of the known formulation of entacapone and the known formulation of levodopa-carbidopa administered concomitantly at the same doses as the present combination composition;

e) the therapeutic effect, such as pharmacokinetics, e.g. bioavailability, achieved with a combination composition of the invention of the dose of 200 mg entacapone/ 250 mg levodopa/25 mg carbidopa is comparable to that of the known formulation of entacapone and the known formulation of levodopa-carbidopa administered concomitantly at the same doses as the present combination composition.

Entacapone alone is available as a tablet where the granulation method used is compaction granulation, i.e., COMTESS® and COMTAN®. When the compaction granulation is used, large amounts of excipients are needed to obtain compressible granules and tablets having the desired, fast, dissolution behavior of an immediate release formulation. The compactability of entacapone is sufficient to allow the preparation of a 200 mg tablet that is still relatively easy to swallow. Applicants found that the compactability of the fixed dose combination tablets is surprisingly worse than that of entacapone alone. Using polyethylene glycol as a compression aid improves the compactability but, on the other hand as stated above, the use of the surface-active agent was found to produce tablets unstable in storage. Also the size of the fixed dose combination tablet comprising entacapone, levodopa and carbidopa prepared by compaction granulation can become too large especially for parkinsonism patients who have difficulties in swallowing.

The invention thus provides an advantageous process for preparing an oral solid composition of the invention, wherein the method comprises a) mixing pharmacologically effective amounts of entacapone and levodopa, or pharmaceutically acceptable salts or hydrates thereof, with at least one pharmaceutically acceptable excipient and optionally a disintegrant to obtain a first mixture; b) granulating the first mixture to obtain a first granule batch; c) mixing a pharmacologically effective amount of carbidopa, or a pharmaceutically acceptable salt or hydrate thereof, with at least one pharmaceutically acceptable excipient and optionally a disintegrant to obtain a second mixture; d) granulating the second mixture to obtain a second granule batch; e) mixing the first granule batch, the second granule batch, a lubricant, and optionally one or more pharmaceutically acceptable excipients, to obtain a third mixture; and f) formulating the third mixture into a plurality of dosage forms, for example, compressing the third mixture into a plurality of tablets, and optionally coating the tablets.

An oral solid composition according to the invention can also be prepared by a) mixing pharmacologically effective amounts of entacapone and levodopa, or pharmaceutically acceptable salts or hydrates thereof, with at least one pharmaceutically acceptable excipient and optionally a disintegrant to obtain a first mixture; b) granulating the first mixture to obtain a plurality of granules; c) adding a pharmacologically effective amount of carbidopa, or a pharmaceutically acceptable salt or hydrate thereof, a lubricant and optionally one or more pharmaceutically acceptable excipients, to the granules to obtain a second mixture; and d) formulating the second mixture into a plurality of dosage forms, for example, compressing the second mixture into a plurality of tablets, and optionally coating the tablets.

The mixing step before granulation can be conducted, e.g., in a tumbler mixer or in a fluidized bed, but preferably in a high shear mixer in a manner known in the art. When wet granulation is used to prepare the granules, the obtained granules are dried, if necessary, before the following step. The granules may be dried, e.g., in a fluidized bed. The tablets are preferably coated with e.g. a HPMC-coating. Preferably the coating contains color pigments, e.g. iron oxide.

By using the process of the invention tablet compositions of the invention may be made which are particularly small for the dosages contained therein and are convenient to administer. These may be any of a wide variety of shapes, although an oval form is preferred. The small size is particularly surprising in view of the size of the presently commercialized COMTAN®/COMTESS® entacapone tablet and in view of the fact that entacapone is difficult to compress and still give an acceptable release, especially in the presence of levodopa and carbidopa. Furthermore, we have found that the compositions of the invention surprisingly have especially good flowability properties.

In another aspect the present invention provides an oral pharmaceutical tablet comprising 200 mg entacapone, 50–150 mg levodopa, and 10–37.5 mg carbidopa and having preferably substantially the following characteristics:

weight 400–750 mg, e.g. 550–590 mg, volume dimensions for oval tablet preferably from 200 to 1000 $mm^3$, e.g. 250 to 800 $mm^3$, such as 300 to 600 $mm^3$, e.g. 300 to 550 $mm^3$.

In yet a further aspect the present invention provides an oral pharmaceutical tablet comprising 200 mg entacapone, 50–150 mg levodopa, and 10–37.5 mg carbidopa and having substantially the following characteristics:

weight 400–750 mg, e.g. 550–590 mg, volume dimensions for oval tablet preferably, length 13–18 mm, e.g. 14–18 mm, width 6–9 mm, height 4–7 mm, e.g. 5–6 mm.

The tablet form of the invention is, of course, not limited to the oval form, but the form can vary e.g. within the given range of volume dimensions.

Insofar as the details of the pharmaceutical excipients are not specifically described herein, they are further described in the handbooks of pharmaceutical excipients known in the art, e.g. in the Handbook of Pharmaceutical Excipients, $2^{nd}$ Edition, Ed. A.H.Kibbe, American Pharmaceutical Association, 1994, and in manufacturer's brochures, the contents of which are incorporated herein by reference.

The invention will be further clarified by the following non-limiting examples.

The excipients used in the formulations of the examples are commercially available: e.g. croscarmellose sodium was a brand Ac-Di-Sol (from FMC Corporation), sodium starch glycolate was a brand Primojel (from Avebe B.A), povidone a brand Kollidon K 30 (from Basf AG) and colloidal silicon dioxide a brand Aerosil 220 (from Degussa AG). Maize starch was from Cerestar Scandinavia and mannitol from Roquette Freres.

EXAMPLE 1

The absorptions of entacapone, levodopa, and carbidopa from entacapone/levodopa/carbidopa 200/100/25 mg tablet formulations containing different excipients and prepared by different methods were tested after a single oral dose in 15 healthy volunteers. The tablets were prepared by wet granulating all the active agents at the same time (Formulation 1) and by compaction granulating all the active agents at the same time (Formulation 2). The formulations were as described in Table 1.

The absorption study was designed to assess the absorption of the active substances between two fixed dose combination tablets and an entacapone 200 mg tablet administered together with a levodopa/carbidopa 100/25 mg tablet, i.e., SINEMET PLUS® distributed in Europe by DuPont Pharmaceuticals Ltd. The study was performed according to an open randomized cross-over design. The plasma entacapone, levodopa, and carbidopa concentrations were determined by two separate reversed-phase HPLC methods, i.e., the entacapone concentrations were measured by one method and the levodopa and carbidopa concentrations by another method.

The results are shown in FIGS. 1–3.

TABLE 1

Compositions of entacapone/levodopa/carbidopa 200/100/25 mg tablet formulations in the first pilot absorption study.

| Core tablet: | Formulation 1 (wet granulation, all in one) mg/tabl. | Formulation 2 (compaction granulation, all in one) mg/tabl. |
|---|---|---|
| Entacapone | 200.0 | 200.0 |
| Levodopa | 100.0 | 100.0 |
| Carbidopa monohydr. (respond carbidopa 25.0 mg) | 27.0 | 27.0 |
| Microcrystalline cellulose | 75.0 | 180.0 |
| Macrogol. 6000 | — | 90.0 |
| Maize starch | 75.0 | — |
| Sodium starch glycolate | 27.0 | — |
| Croscarmellose sodium | — | 30.0 |
| Povidone | 36.0 | — |
| Microcrystalline cellulose | 49.2 | — |
| Colloidal silicon dioxide | 1.8 | — |
| Magnesium stearate | 9.0 | 13.0 |
| Theoretical weight of the tablet core | 600.0 | 640.0 |
| Coating | HPMC-coating containing color pigments | HPMC-coating containing color pigments |
| Theoretical weight of the coated tablet | 619.5 | 660.0 |
| Manufacturing of granules | All the active substances were high shear granulated together | all the active substances were compaction granulated together |

EXAMPLE 2

Examples of suitable entacapone/levodopa/carbidopa 200/100/25 mg tablet formulations are described in Table 2. The tablets were prepared by adding carbidopa separately as granules (Formulation 3) and as such in a powder form (Formulation 4) into the formulation. Accordingly, for preparing Formulation 3, entacapone and levodopa were wet granulated together with maize starch, mannitol, croscarmellose sodium and povidone in a conventional high shear mixer. Carbidopa was wet granulated separately with maize starch, mannitol, croscarmellose sodium and povidone in a high shear mixer. The dry entacapone/levodopa-granules, the dry carbidopa granules, croscarmellose sodium, mannitol and magnesium stearate were mixed together and the mass obtained was compressed to tablets with an oval shape and coated with HPMC-coating containing a color pigment. Formulation 4 was prepared analogously with Formulation 3 except carbidopa was added as such in a powder form.

The absorptions of formulations 3 and 4 were tested in 15 healthy volunteers after a single oral dose. The reference was an entacapone 200 mg tablet, COMTESS®, administered together with a levodopa/carbidopa 100/25 mg tablet, SINEMET® PLUS, distributed in UK by DuPont Pharmaceuticals Ltd. The study was performed according to an open randomized cross-over design. The plasma entacapone, levodopa, and carbidopa concentrations were determined by two separate reversed-phase HPLC methods, i.e., the entacapone concentrations were measured by one method and the levodopa and carbidopa concentrations by another method.

According to the results shown in FIGS. 4–6 the absorptions of the tested two formulations are comparable to the commercial reference formulations. The dissolved amounts of entacapone, levodopa and carbidopa are at least 50% in 30 minutes when measured with USP dissolution equipment.

TABLE 2

Compositions of entacapone/levodopa/carbidopa 200/100/25 mg tablet formulations (separate carbidopa in the formulations).

|  | Formulation 3 (mg) | Formulation 4 (mg) |
|---|---|---|
| Entacapone | 200.0 | 200.0 |
| Levodopa | 100.0 | 100.0 |
| Carbidopa monohydrate | 27.0 | 27.0 |
| Maize Starch | 85.0 | 75.0 |
| Mannitol | 86.1 | 44.0 |
| Croscarmellose sodium | 23.7 | 20.0 |
| Povidone | 39.7 | 36.0 |
| Magnesium stearate | 8.5 | 8.0 |
| Theoretical weight of the core tablet | 570.0 | 510.0 |
| HPMC-coating containing color pigments | 17.0 | 15.0 |
| Theoretical weight of the coated tablet | 587.0 | 525.0 |
| Manufacturing of Granules | Entacapone/Levodopa Granules and Carbidopa Granules were Manufactured Separately in a high shear mixer | Entacapone/Levodopa granules were manufactured in a high shear mixer. Carbidopa was added as such to the granules together with tabletting excipients |

The oval tablets compressed from the tablet mixtures had the following dimensions:
Formulation 3 (length of 16.4 mm; width of 7.7 mm and height of 5.7 mm) and
Formulation 4 (length of 16.4 mm; width of 7.7 mm and height of 5.1 mm)

EXAMPLE 3

The following Formulations 5 and 6 shown in TABLE 3 were prepared according to the procedure of Formulation 3, but using entacapone/levodopa/carbidopa in amounts of 200 mg/50 mg/1 2.5 mg (Formulation 5) and, resp., 200 mg/150 mg/37.5 mg (Formulation 6):

TABLE 3

| Name of ingredient | Formulation 5 (mg) | Formulation 6 (mg) |
|---|---|---|
| Entacapone | 200.0 | 200.0 |
| Levodopa | 150.0 | 50.0 |
| Carbidopa monohydrate | 40.5 | 13.5 |
| Maize starch | 105.0 | 65.0 |
| Mannitol | 113.0 | 59.5 |
| Croscarmellose sodium | 28.5 | 17.7 |

TABLE 3-continued

| Name of ingredient | Formulation 5 (mg) | Formulation 6 (mg) |
|---|---|---|
| Povidone | 46.6 | 31.9 |
| Magnesium stearate | 10.5 | 6.5 |
| Core weight | 694 | 444 |

Core tablets are coated with colored HPMC-coating to the weight gain of 2–3%.

An entacapone/levodopa/carbidopa formulation in amounts of 200 mg/100 mg/10 mg can also be prepared using the procedure of Formulation 3.

Those skilled in the art will recognize that while specific embodiments have been illustrated and described, various modifications and changes may be made without departing from the spirit and scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The references discussed herein are specifically incorporated by reference herein in their entirety.

We claim:

1. A stable oral solid composition comprising pharmacologically effective amounts of active agents consisting of entacapone, levodopa, and carbidopa, or pharmaceutically acceptable salts or hydrates thereof, and comprising at least one pharmaceutically acceptable excipient other than microcrystalline cellulose.

2. The composition according to claim 1, wherein the composition is in the form of a tablet.

3. The composition according to claim 1, wherein the composition does not comprise microcrystalline cellulose.

4. The composition according to claim 2, wherein the composition does not comprise microcrystalline cellulose.

5. The composition according to claim 1, wherein the composition comprises at least one pharmaceutically acceptable excipient other than a surface active agent.

6. The composition according to claim 1, wherein the composition comprises at least one pharmaceutically acceptable excipient other than silica.

7. The composition according to claim 1, wherein the composition comprises a disintegrant as the excipient.

8. The composition according to claim 7, wherein the disintegrant is sodium starch glycolate or croscarmellose sodium.

9. The composition according to claim 1, wherein the composition comprises a sugar alcohol as the excipient.

10. The composition according to claim 1, wherein the composition comprises hydrogenated vegetable oil as the excipient.

* * * * *